(12) United States Patent
Bae et al.

(10) Patent No.: US 9,180,458 B2
(45) Date of Patent: Nov. 10, 2015

(54) BIOSENSOR HAVING IDENTIFICATION INFORMATION AND APPARATUS FOR READING IDENTIFICATION INFORMATION OF BIOSENSOR

(75) Inventors: Byeong-woo Bae, Anyang-si (KR); Sung-dong Lee, Yeongcheon-si (KR); Hong-seong Suk, Anyang-si (KR); Jina Yoo, Anyang-si (KR); Ki-won Lee, Pocheon-si (KR); Jong-won Hong, Anyang-si (KR); Duck-sung Nam, Osan-si (KR)

(73) Assignee: Infopia Co., Ltd., Anyang-si (KR)

( * ) Notice: Subject to any disclaimer, the term of this patent is extended or adjusted under 35 U.S.C. 154(b) by 909 days.

(21) Appl. No.: 11/521,046

(22) Filed: Sep. 14, 2006

(65) Prior Publication Data

US 2010/0224487 A1    Sep. 9, 2010

(30) Foreign Application Priority Data

Sep. 16, 2005    (KR) .................. 10-2005-0086905

(51) Int. Cl.
*B01L 3/00*    (2006.01)
*G01N 33/487*    (2006.01)
*G01N 35/00*    (2006.01)

(52) U.S. Cl.
CPC .......... *B01L 3/545* (2013.01); *G01N 33/48771* (2013.01); *G01N 2035/00772* (2013.01)

(58) Field of Classification Search
CPC ............ G01N 33/48771; G01N 27/3272; G01N 2035/00772; G01N 2035/00752; G01N 35/00693; G01N 2035/00118; G01N 2035/00782; B01L 2300/0645
USPC .......................................................... 436/50
See application file for complete search history.

(56) References Cited

U.S. PATENT DOCUMENTS 4,220,016 A * 9/1980 Frenger ........................ 63/14.9
5,108,564 A * 4/1992 Szuminsky et al. ........ 205/777.5

(Continued)

FOREIGN PATENT DOCUMENTS

KR    2003-0004933 A    1/2003
KR    1020030004933 A    1/2003

(Continued)

OTHER PUBLICATIONS

Korean Office Action dated Aug. 18, 2006 for Application No. 10-2005-0086905 ( All references cited in Office Action are cited above).

(Continued)

*Primary Examiner* — Sally Merkling
(74) *Attorney, Agent, or Firm* — NSIP Law

(57) ABSTRACT

A biosensor is provided, including an identification information recording unit having identification information of the biosensor recorded thereon, where the identification information recording unit is a color tag that is attached on the biosensor and indicates the identification information by color, chroma of color, or arrangement pattern of colors. An apparatus for reading identification information of a biosensor is provided, including: a biosensor sensing unit detecting the biosensor; a light-emitting unit emitting light on an identification information recording unit when the biosensor sensing unit detects the biosensor, the identification information recording unit having the identification information of the biosensor recorded thereon; a light-receiving unit that receives the light emitted from the light-emitting unit, and reflected or refracted by or passing through the identification information recording section; and an identification information reading unit analyzing the light received by the light-receiving unit and reading the identification information of the biosensor.

4 Claims, 4 Drawing Sheets

(56) References Cited

U.S. PATENT DOCUMENTS

| | | | |
|---|---|---|---|
| 5,780,294 A * | 7/1998 | Stevens et al. | 435/297.5 |
| 5,945,341 A * | 8/1999 | Howard, III | 436/46 |
| 6,168,957 B1 * | 1/2001 | Matzinger et al. | 436/518 |
| 6,203,069 B1 * | 3/2001 | Outwater et al. | 283/88 |
| 6,298,359 B1 | 10/2001 | Konishi et al. | |
| 6,514,460 B1 | 2/2003 | Fendrock | |
| 6,814,844 B2 * | 11/2004 | Bhullar et al. | 204/403.01 |
| 7,179,654 B2 * | 2/2007 | Verdonk et al. | 436/172 |
| 2002/0123671 A1 * | 9/2002 | Haaland | 600/300 |
| 2002/0132363 A1 | 9/2002 | Rehm | |
| 2002/0137230 A1 * | 9/2002 | Nadaoka et al. | 436/518 |
| 2003/0027342 A1 | 2/2003 | Sheridan et al. | |
| 2004/0146958 A1 | 7/2004 | Bae et al. | |
| 2004/0200721 A1 * | 10/2004 | Bhullar et al. | 204/403.01 |
| 2005/0036913 A1 | 2/2005 | Yamakawa et al. | |
| 2005/0161323 A1 | 7/2005 | Bae et al. | |
| 2006/0163086 A1 | 7/2006 | Bae et al. | |
| 2007/0015286 A1 * | 1/2007 | Neel et al. | 436/149 |

FOREIGN PATENT DOCUMENTS

| | | |
|---|---|---|
| KR | 2003-0090025 A | 11/2003 |
| KR | 10-2004-0028437 A | 4/2004 |
| KR | 1020040028437 A | 4/2004 |
| KR | 200522644 | 3/2005 |
| KR | 10-2005-0122078 A | 12/2005 |
| KR | 1020050122078 A | 12/2005 |
| KR | 10-2006-0009665 A | 2/2006 |
| KR | 1020060009665 A | 2/2006 |
| WO | 2005012900 | 2/2005 |

OTHER PUBLICATIONS

European Search Report for Application 06019179.8 - 1240/1764153, issued on May 3, 2010. All references cited therein and not previously submitted, are submitted herewith.

First Notification of Office Action from the State Intellectual Property Office of P.R. China, dated Oct. 20, 2010, for Application No. 200610127443.2.

European Search Report—European Application No. 12007348.1 issued on Jan. 14, 2013, citing US2002/132363, WO2005/012900, US20041200721 and U.S. Pat. No. 6168957.

European Search Report—European Application No. 12007347.3 issued on Jan. 14, 2013, citing US2004/200721, WO20051012900 and U.S. Pat. No. 6168957.

Request for appeal against a decision to reject an application filed with the Korean Intellectual Property Office.

European Office Action issued on Apr. 24, 2014, in counterpart European Patent Application No. 12007347.3 (4 pages, in English).

European Office Action issued on Apr. 24, 2014, in counterpart European Patent Application No. 12007348.1 (4 pages, in English).

* cited by examiner

BIOSENSOR HAVING IDENTIFICATION INFORMATION AND APPARATUS FOR READING IDENTIFICATION INFORMATION OF BIOSENSOR

CROSS-REFERENCE TO RELATED APPLICATION(S)

This application claims the benefit under 35 USC 119(a) of Korean Patent Application No. 10-2005-0086905 filed on Sep. 16, 2005, in the Korean Intellectual Property Office, the disclosure of which is incorporated herein in its entirety by reference.

BACKGROUND OF THE INVENTION

1. Field of the Invention

The present invention relates to a biosensor having identification information recorded thereon and an apparatus for reading identification information of a biosensor and, more particularly, to a technology of reading biosensor information, such as the kind and manufacturer of biosensor, from the biosensor.

2. Description of Related Art

US Patent Application Publication No. US 2004/200721 published on Oct. 14, 2004 discloses a biosensor with a code pattern in which an identification information recording means is attached on the biosensor to record identification information of the biosensor, and biosensor information, such as the kind and manufacturer of biosensor, is read from the identification information recorded on the recording means.

In the above-mentioned US patent application Publication, the biosensor information is recorded in barcode form and is read by a barcode reader.

However, there is a problem in that since the barcode is used as an identification information recording means of the biosensor, the production cost of the biosensor rises.

SUMMARY OF THE INVENTION

The present invention provides a biosensor having a color tag having identification information of the biosensor, and an apparatus for reading the identification information of the biosensor.

According to an aspect of the present invention, there is provided a biosensor including an identification information recording unit having identification information of the biosensor recorded thereon, where the identification information recording unit is a color tag that is attached on the biosensor and indicates the identification information by color.

According to another aspect of the present invention, there is provided a biosensor including an identification information recording unit having identification information of the biosensor recorded thereon, where the identification information recording unit is a color tag that is attached on the biosensor and indicates the identification information by chroma of color.

According to another aspect of the present invention, there is provided a biosensor including an identification information recording unit having identification information of the biosensor recorded thereon, where the identification information recording unit is a color tag that is attached on the biosensor and indicates the identification information by arrangement pattern of colors.

The biosensor may be an electro-chemical biosensor.
The biosensor may be a photochemical biosensor.

According to another aspect of the present invention, there is provided an apparatus for reading identification information of a biosensor, including: a biosensor sensing unit that detects the biosensor; a light emitting unit that emits light on an identification information recording unit when the biosensor sensing unit detects the biosensor, the identification information recording unit having the identification information of the biosensor recorded thereon; a light receiving unit that receives the light emitted from the light emitting unit, and reflected or refracted by or passing through the identification information recording section; and an identification information reading unit that analyzes the light received by the light receiving unit and reads the identification information of the biosensor.

The apparatus may further include an identification information output unit that outputs the identification information read by the identification information reading unit.

The identification information output unit may output the identification information to a display device.

The identification information output unit may output the identification information to a communication terminal connected to a network.

The identification information output unit may output the identification information to a printer.

The identification information output unit may output the identification information to a memory device.

The identification information reading unit may include: an A/D conversion unit that converts an analog light signal received by the light receiving unit into a digital signal; and a signal analysis unit that analyzes the digital signal converted by the A/D conversion unit and reads the identification information of the biosensor.

The identification information reading unit may further include an amplification unit that amplifies the analog light signal received by the light receiving unit and outputs the amplified signal to the A/D conversion unit.

The identification information may contain at least one of type of the biosensor, manufacturer of the biosensor, and correction code used to correct measurement results.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Exemplary embodiments in accordance with the present invention will now be described in detail with reference to the accompanying drawings.

A biosensor 100 having identification information recorded thereon includes an identification information recording unit 110 that is placed on the biosensor 100 and has identification information of the biosensor 100. A color tag is used as the identification information recording unit 110.

Examples of the identification information include the kind of biosensor, manufacturer of biosensor, correction code used to correct measurement results, and serial number.

The correction code is used to correct different measurement results of different biosensors that are tested under the same conditions.

Figure 1:
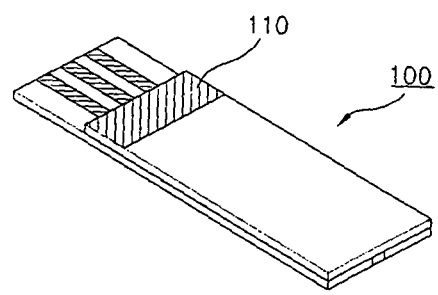
FIG. 1 is a perspective view of a biosensor having identification information recorded thereon according to an embodiment of the present invention.
Figure 2:
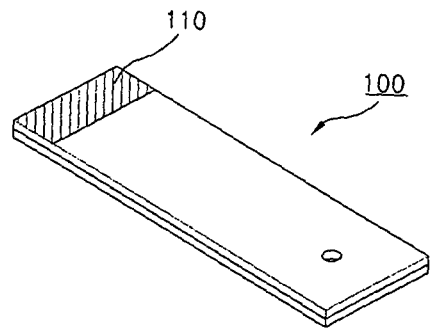
FIG. 2 is a perspective view of a biosensor having identification information recorded thereon according to an embodiment of the present invention.

The color tag can be generally applied to biosensors, such as an electro-chemical biosensor shown in FIG. 1 or a photochemical biosensor shown in FIG. 2.

The electro-chemical biosensor is configured so as to obtain measurement results by reading current applied to electrodes upon injection of a sample. Korean Patent Application Nos. 2001-40690 filed on Jul. 7, 2001, 2002-27971 filed on May 20, 2002, 2002-59612 filed on Sep. 30, 2002, and 2004-47228 filed on Jun. 23, 2004 disclose the electro-chemical biosensor and a detailed description thereof will thus be omitted herein.

The photochemical biosensor is configured so as to obtain measurement results by optically analyzing antigen-antibody reaction produced by injection of a sample by immuno-chromatography. Korean Patent Application No. 2004-58332 filed on Jul. 26, 2004 discloses the photochemical biosensor and a detailed description thereof will thus be omitted herein.

The color tag is attached on the biosensor 100, and is configured so as to record identification information of the biosensor 100 in the following methods.

First, the identification information of the biosensor 100 may be represented by colors of the color tag.

For instance, the color tag may be configured such that the color tag having a color of red indicates a biosensor for blood glucose measurement that is manufactured by 'A' company, and a color of yellow indicates a biosensor for hemoglobin measurement that is manufactured by 'B' company. That is, the identification information of biosensor is recorded by colors of the color tag.

Secondly, the identification information of the biosensor 100 may be represented by chroma of colors constituting the color tag.

For instance, the color tag may be configured such that the color tag having a color of red and a chroma of a reference value or more indicates a biosensor for blood glucose measurement that is manufactured by 'A' company, one having a color of red and a chroma of less than the reference value indicates a biosensor for hemoglobin measurement that is manufactured by 'A' company, one having a color of yellow and a chroma of a reference value or more indicates a biosensor for blood glucose measurement that is manufactured by 'B' company, one having a color of yellow and a chroma of less than the reference value indicates a biosensor for hemoglobin measurement that is manufactured by 'B' company. That is, the identification information of biosensor is recorded by the chroma of colors constituting the color tag.

Thirdly, the identification information of the biosensor 100 may be represented by arrangement of colors constituting the color tag.

Figure 3:
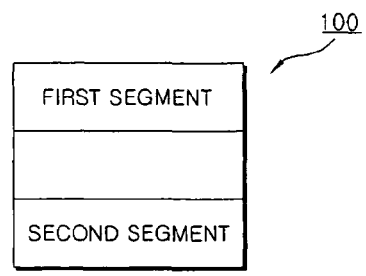
FIG. 3 is a color tag of a biosensor having identification information recorded thereon according to an embodiment of the present invention.

For instance, as shown in FIG. 3, the color tag may be configured such that the color tag has first and second segments in which the first segment having a color of red indicates a biosensor manufactured by 'A' company, the first segment having a color of yellow indicates one manufactured by 'B' company, the second segment having a color of red indicates a biosensor for blood glucose measurement, and the second segment having a color of yellow indicates a biosensor for hemoglobin measurement. That is, the identification information of biosensor is recorded by the arrangement of colors constituting the color tag.

Accordingly, the biosensor having the identification information recorded thereon according to an embodiment of the present invention employs the color tag having the identification information of the biosensor, in which the identification information is read by the following apparatus for reading the identification information by analyzing the identification information by an optical method. Accordingly, it is possible to record and read the identification information of the biosensor at a lower cost.

Figure 4:
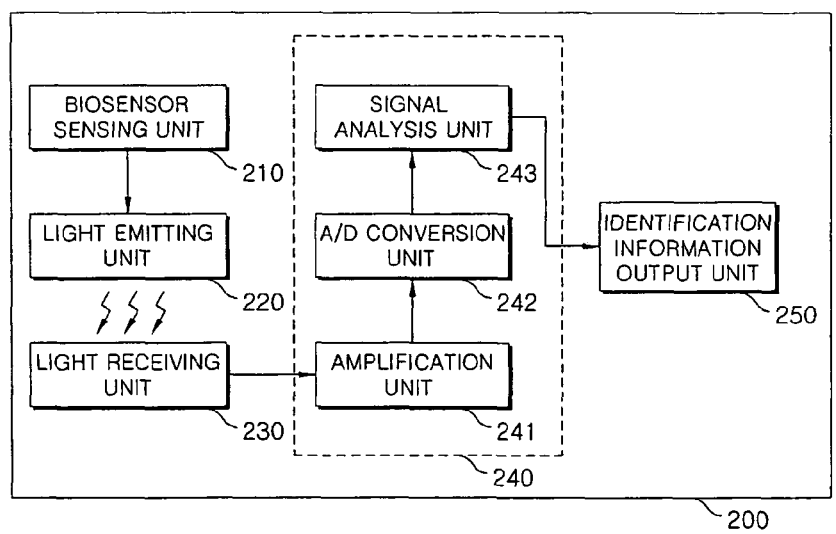
FIG. 4 is a block diagram of an apparatus for reading identification information of a biosensor according to an embodiment of the present invention.

FIG. 4 is a block diagram of an apparatus for reading identification information of a biosensor according to an embodiment of the present invention.

An apparatus 200 for reading identification information of a biosensor includes a biosensor sensing unit 210, a light emitting unit 220, a light receiving unit 230, and an identification information reading unit 240. The reading apparatus 200 may be unitarily formed with or separately from an apparatus for measuring sample reaction results of the biosensor.

The biosensor sensing unit 210 detects the biosensor 100.

In a case where the reading apparatus 200 is configured in such a manner that the biosensor 100 is inserted into the reading apparatus 200, the biosensor sensing unit 210 detects low or high voltage applied upon inserting the biosensor 100 into the reading apparatus 200, such that the reading apparatus 200 senses whether or not the biosensor 100 is inserted into the reading apparatus 200.

When the biosensor 100 is detected by the biosensor sensing unit 210, the light emitting unit 220 emits light to an identification information recording unit of the biosensor 100, i.e., color tag.

The light receiving unit 230 receives light that is emitted by the light emitting unit 220 and reflected or refracted by or passes through the color tag.

The identification information reading unit 240 analyzes the light received by the light receiving unit 230, and reads the identification information, such as the kind and manufacturer of the biosensor 100, correction code used to correct measurement results, and serial number.

Different biosensors have different measurement results even though they are tested under the same condition. The reading apparatus 200 or the measurement apparatus for measuring sample reaction results of the biosensor refers to the correction code to compensate for the different measurement results. In this case, the reading apparatus 200 or measurement apparatus may include a memory unit for storing correction functions or correction tables that are referenced by the correction code.

The identification information reading unit 240 includes an amplification unit 241, an A/D conversion unit 242, and a signal analysis unit 243.

The amplification unit 241 amplifies an analog light signal received by the light receiving unit 230 and outputs it to the A/D conversion unit 242.

The A/D conversion unit 242 converts the analog light signal into a digital signal.

The signal analysis unit 243 analyzes the digital signal and reads the identification information of the biosensor.

The signal analysis unit 243 reads the identification information in the following manner.

First, the identification information of the biosensor can be read by colors of color tag.

For example, the color tag having a color of red indicates a biosensor for blood glucose measurement that is manufactured by 'A' company, and the color tag having a color of yellow indicates one for hemoglobin measurement that is manufactured by 'B' company.

Secondly, the identification information of the biosensor can be read by the chroma of color of the color tag.

For instance, a color tag having a color of red with a chroma of not less than a reference value indicates a biosensor for blood glucose measurement of 'A' company, a color tag having a color of red with a chroma of less than the reference value indicates a biosensor for hemoglobin measurement of 'A' company, a color tag having a color of yellow with a chroma of not less than the reference value indicates a biosensor for blood glucose measurement of 'B' company, and a color tag having a color of yellow with a chroma of less than the reference value indicates a biosensor for hemoglobin measurement of 'B' company.

Thirdly, the arrangement pattern of colors contained in the color tag is used to record the identification information of the biosensor 100.

In a case where the color tag has two segments, i.e., first and second segments, as shown in FIG. 3, the color tag may be configured such that the first segment having a color of red indicates a biosensor manufactured by 'A' company, the first segment having a color of yellow indicates one manufactured by 'B' company, the second segment having a color of red indicates a biosensor for blood glucose measurement, and the second segment having a color of yellow indicates one for hemoglobin measurement.

Accordingly, the apparatus for reading the identification information of a biosensor according to an embodiment of the present invention can read the identification information of the biosensor at a lower cost since it analyzes and reads the color tag attached on the biosensor containing the identification information by an optical method.

The apparatus 200 for reading the identification information of biosensor may further include an identification information output unit 250.

The identification information output unit 250 outputs the identification information of biosensor read by the identification information reading unit 240 to a display unit, communication terminal, printer, memory unit and other terminals so that users can monitor the identification information.

Operation of the apparatus 200 for reading the identification information of the biosensor will be described in detail with reference to FIGS. 5 and 6.

Figure 5:
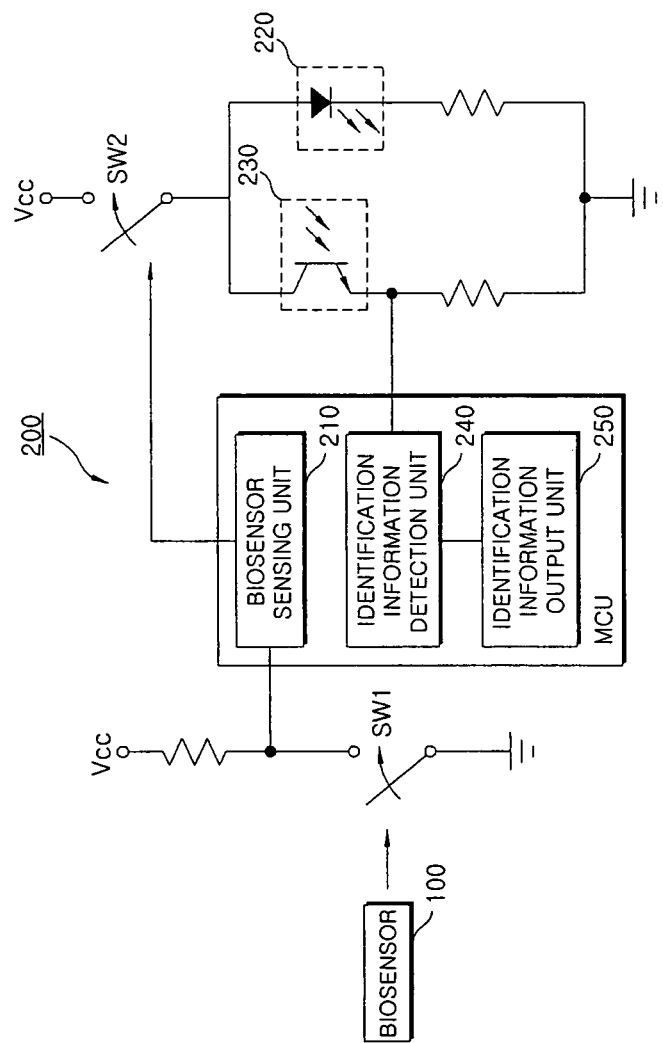
FIG. 5 is a circuit diagram of an apparatus for reading identification information of a biosensor according to an embodiment of the present invention.

FIG. 5 is a circuit diagram of an apparatus for reading the identification information of biosensor according to an embodiment of the present invention. In this case, a light-emitting diode (LED) is used as the light emitting unit 220 and a phototransistor is used as the light receiving unit 230.

When the biosensor 100 is inserted into the apparatus 200 for reading the identification information, a switch SW1 is switched on and a low-level voltage is applied to a micro control unit (MCU).

When the low-level voltage is applied to the MCU, the biosensor sensing unit 210 incorporated in the MCU determines that the biosensor 100 has been inserted into the reading apparatus 200. The biosensor sensing unit 210 outputs a control signal to a switch SW2 to be switched on, and applies voltage Vcc to the LED and phototransistor.

At this time, light is emitted by the LED, and input to an identification information recording means, i.e., color tag, having the identification information of the biosensor recorded thereon. The light is reflected or refracted by or passing through the color tag and received by the phototransistor.

After the phototransistor receives the light, the identification information reading unit 240 incorporated in the MCU analyzes the light, reads and outputs the identification information of the biosensor 100 through the identification information output unit 250 to a display unit, communication terminal, printer, memory unit, and other terminals. Accordingly, it is possible to read the identification information of the biosensor 100 at a lower cost.

Figure 6:
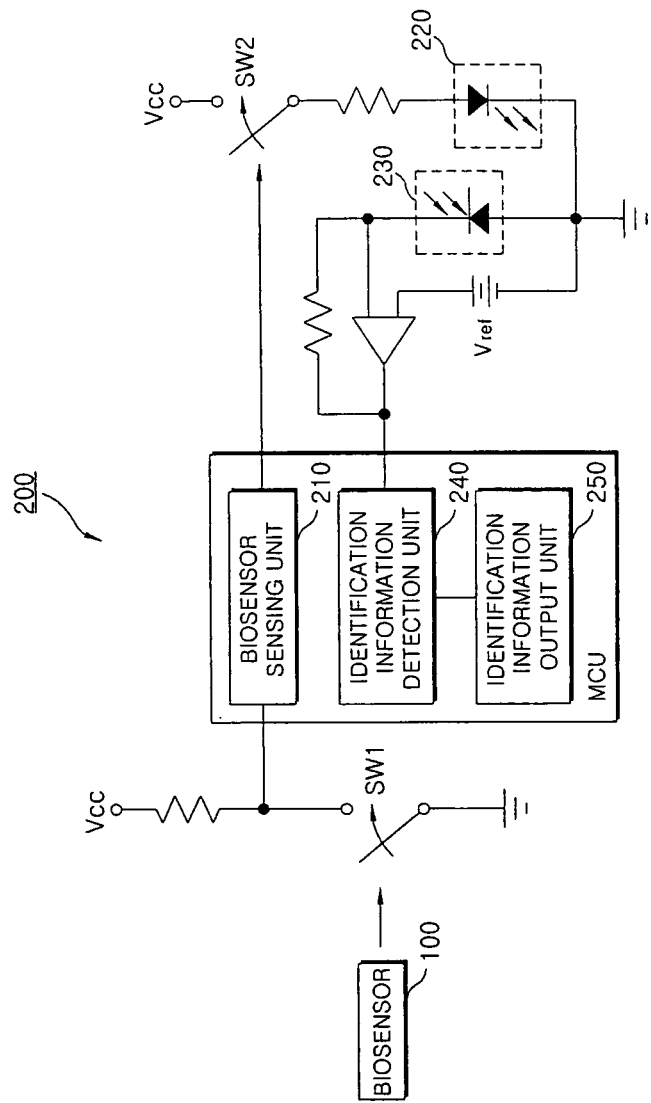
FIG. 6 is a circuit diagram of an apparatus for reading identification information of a biosensor according to an embodiment of the present invention.

FIG. 6 is a circuit diagram of an apparatus for reading identification information of a biosensor according to an embodiment of the present invention. In this case, a LED is used as the light emitting unit 220 and a photodiode is used as the light receiving unit 230.

When the biosensor 100 is inserted into the apparatus 200 for reading the identification information, a switch SW1 is switched on and a low-level voltage is applied to a MCU.

When the low-level voltage is applied to the MCU, the biosensor sensing unit 210 incorporated in the MCU determines that the biosensor 100 has been inserted into the reading apparatus 200. The biosensor sensing unit 210 outputs a control signal to a switch SW2 to be switched on, and applies voltage Vcc to the LED and photodiode.

At this time, light is emitted by the LED, and input to an identification information recording means, i.e., color tag. The light is reflected or refracted by or passing through the color tag, and received by the photodiode.

After the photodiode receives the light, the identification information reading unit 240 incorporated in the MCU analyzes the light, reads and outputs the identification information of the biosensor 100 through the identification information output unit 250 to a display unit, communication terminal, printer, memory unit, and other terminals. Accordingly, it is possible to read the identification information of the biosensor 100 at a lower cost.

As apparent from the above description, the biosensor having the identification information recorded thereon and the apparatus for reading the identification information of the biosensor can record and read the identification information of the biosensor, such as the kind and manufacture of the biosensor, correction code, and serial number, at a lower cost by attaching the color tag having the identification information on the biosensor and reading the identification information from the color tag by the optical method.

While the present invention has been described with reference to exemplary embodiments thereof, it will be understood by those skilled in the art that various changes in form and details may be made therein without departing from the scope of the present invention as defined by the following claims.

What is claimed is:

1. An electro-chemical biosensor comprising:
   an electro-chemical biosensor element comprising electrodes and configured to obtain measurement results by reading current applied to the electrodes upon introduction of a blood sample; and
   an identification information recording unit comprising two or more non-overlapping color segments on a surface of the electro-chemical biosensor element, each of the color segments presenting color on a single layer, the color segments being arranged and configured so that a combination of respective colors of the color segments regardless of shapes of the color segments provides optically readable identification information of the electro-chemical biosensor element;

wherein the optically readable identification information comprises any one or any combination of a type of the electro-chemical biosensor element and a correction code used to correct the measurement results obtained by the electro-chemical biosensor element.

2. The electro-chemical biosensor of claim 1, wherein the two or more color segments each comprise a chroma of color.

3. The electro-chemical biosensor of claim 1, wherein the identification information recording unit comprises a color tag attached to the electro-chemical biosensor element; and the color tag comprises the two or more color segments.

4. The electro-chemical biosensor of claim 1, wherein each of the color segments is configured to present the color on the single layer independent of the measurement results obtained by the electro-chemical biosensor element.

* * * * *